US009432760B2

(12) United States Patent
Iseberg et al.

(10) Patent No.: US 9,432,760 B2
(45) **Date of Patent: *Aug. 30, 2016**

(54) CONFORMABLE EARTIP

(71) Applicant: Etymotic Research, Inc., Elk Grove Village, IL (US)

(72) Inventors: Steve Iseberg, Crystal Lake, IL (US); Steve Viranyi, Palatine, IL (US)

(73) Assignee: ETYMOTIC RESEARCH, INC., Elk Grove Village, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/877,460

(22) Filed: Oct. 7, 2015

(65) Prior Publication Data

US 2016/0029112 A1 Jan. 28, 2016

Related U.S. Application Data

(63) Continuation of application No. 14/475,928, filed on Sep. 3, 2014, now Pat. No. 9,197,956.

(60) Provisional application No. 61/873,690, filed on Sep. 4, 2013.

(51) Int. Cl.
*A61B 7/02* (2006.01)
*H04R 1/10* (2006.01)

(52) U.S. Cl.
CPC .................................. *H04R 1/1016* (2013.01)

(58) Field of Classification Search
CPC .................................................... H04R 25/652
USPC .................................................. 181/135, 130
See application file for complete search history.

(56) References Cited

U.S. PATENT DOCUMENTS

| | | | | |
|---|---|---|---|---|
| 5,833,367 | A | 11/1998 | Cheslock et al. | |
| 5,954,669 | A * | 9/1999 | Iseberg | 600/559 |
| 7,681,577 | B2 | 3/2010 | Blanchard | |
| 8,348,010 | B2 | 1/2013 | Stiehl et al. | |
| D698,023 | S * | 1/2014 | Iseberg et al. | D24/174 |
| 9,197,956 | B2 * | 11/2015 | Iseberg et al. | |
| 2009/0103764 | A1 | 4/2009 | Stiehl et al. | |
| 2011/0051979 | A1 | 3/2011 | Lee et al. | |
| 2012/0191004 | A1 * | 7/2012 | Iseberg et al. | 600/559 |
| 2014/0138179 | A1 | 5/2014 | Burton | |
| 2014/0166389 | A1 | 6/2014 | Young-Mun | |
| 2014/0251716 | A1 | 9/2014 | Saltykov | |

* cited by examiner

*Primary Examiner* — Forrest M Phillips
(74) *Attorney, Agent, or Firm* — McAndrews, Held & Malloy, Ltd.

(57) ABSTRACT

Certain embodiments provide a conformable eartip. The conformable eartip includes a round flange and a core. The round flange includes a sealing surface for mating with walls of an ear canal. The round flange extends from an insertion end to an opposite end of the conformable eartip. The sealing surface is tapered from the opposite end toward the insertion end of the conformable eartip. The core is joined to the round flange at the insertion end of the conformable eartip. The core extends from the insertion end to a base of the core toward the opposite end of the conformable eartip. The core includes a channel extending through the core from the insertion end of the conformable eartip to the base of the core. In various embodiments, the conformable eartip provides an elongation ratio of at least 1.4 and/or a compression ratio of at least 2.0.

13 Claims, 11 Drawing Sheets

CONFORMABLE EARTIP

CROSS-REFERENCE TO RELATED APPLICATIONS/INCORPORATION BY REFERENCE

This application is a continuation of U.S. patent application Ser. No. 14/475,928, entitled "Conformable Eartip," filed on Sep. 3, 2014, which makes reference to, claims priority to, and claims benefit from U.S. Provisional Patent Application Ser. No. 61/873,690, entitled "Conformable Eartip," filed on Sep. 4, 2013. The entire contents of each above-mentioned prior-filed application is hereby expressly incorporated herein by reference.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention relates to an eartip that conforms to the various shapes of human ear canals and provides an acoustic and pressure seal to the ear canal. More specifically, the present invention provides an eartip that seals to ear canals quicker, easier, and more comfortably than existing eartips. The conformable eartip provides a low coefficient of friction so that the eartip inserts into the ear canal without discomfort and allows for direct insertion into the ear canal without requiring preparatory compression of the foam. The conformable eartip creates a minimal amount of pressure against the ear canal when inserted, has the ability to significantly distort its shape to easily conform to non-circular ear canal shapes, conforms to bends in an ear canal, and provides a seal at varying depths within an ear canal.

There are three common categories of commercially available eartips, compressible foam, elastomeric, and custom earmolds. Compressible foam tips are nominally round foam cylinders that seal to the ear canal through compressibility of the foam. Compressible foam eartips are generally pre-formed by compressing the foam to reduce the outer diameter, allowing the tip to enter the ear canal before recovery of the foam to its relaxed diameter. As the foam expands in the ear canal it seals against the surface of the ear canal walls. Compressible foam eartips are often made of slow-recovery foam allowing for time between manually pre-compressing the foam and inserting it into the ear canal. A disadvantage of compressible foam eartips is that the eartips typically require the user to compress the foam prior to insertion into the ear canal.

Another common problem with compressible foam eartips is that the expansion of the foam in the ear canal can cause significant pressure against the ear canal wall. The excessive pressure against the ear canal wall may cause discomfort for a user of the eartip. Additionally, many existing compressible foam eartips do not conform to bends in an ear canal when attached to a sound tube of a hearing device. The inability of compressible foam eartips to conform to bends in an ear canal may prevent the eartips from providing a seal, particularly at deeper insertion depths. At shorter insertion depths, compressible foam eartips can be ineffective for excluding noise and can increase the amount of occlusion effect a user experiences when talking. A further disadvantage of existing compressible foam eartips is that a greater diameter of foam is typically needed to completely seal non-circular ear canals because the foam does not appreciably expand outward during recovery to its relaxed diameter.

Elastomer eartips are nominally round forms that are generally directly inserted into the ear canal without pre-compression. A common problem with elastomer eartips is that friction between the eartip and the ear canal wall can make the insertion of the eartip more difficult and less comfortable. A lubricant applied to the eartip can provide a reduction of friction but is seldom used because it can be messy and/or inconvenient. Additionally, existing elastomer eartips do not easily conform to the ear canal, which may cause significant pressure against the ear canal wall. The excessive pressure against the ear canal wall can cause discomfort for the user of the eartip.

Another disadvantage of existing elastomer eartips is that the eartips have difficulty sealing to the varying shapes of human ear canals. For example, many elastomer eartips may crease inward when inserted in non-circular ear canals thereby preventing a seal from forming between the eartip and the ear canal. Many existing elastomer eartips include thick and/or otherwise large core sections that inhibit the eartips ability to conform to bends in an ear canal. The inability of existing elastomer eartips to conform to bends in an ear canal may prevent a seal from forming between the eartips and the ear canal and/or can cause discomfort to a wearer because the ear canals may be forced to conform to the eartips. Also, elastomer eartips typically require deep insertion due to the nominal size of the eartips relative to the ear canal and the lack of conformability of the eartips. The ability to achieve a seal without deep insertion to the ear canal is particularly beneficial when the user is uncomfortable with inserting eartips into their ear canal, or for those where a deeper insertion is in itself uncomfortable.

Some elastomer eartips provide multiple sealing surfaces in incrementally increasing diameters, intended to allow the eartip to seal to a larger range of eartip diameters. Although multi-flange elastomer eartips may seal to a large variety of ear canal sizes, a significantly deeper insertion is typically needed for larger size ear canals and the insertion depth with smaller size ear canals may be limited. Another disadvantage of the multi-flange elastomer eartip style is a longer minimum length to accommodate the multiple sealing surfaces.

Custom earmolds are derived from a measurement or mold of the individual ear canal and are typically produced using silicone materials. Custom earmolds properly fit only the ear canal for which it was made, sealing to the ear canal by mating exactly with the ear canal shape. A common problem with custom earmolds is that friction between the material and the ear canal wall can make the insertion of the eartip more difficult and less comfortable. A lubricant applied to the eartip can provide a reduction of friction but is seldom used because it can be messy and/or inconvenient. Other problems with existing custom earmolds include the high cost of custom earmolds, the additional time needed for fitting and manufacturing the custom earmolds, and the inability to vary the insertion depth of the custom earmolds.

Further limitations and disadvantages of conventional and traditional approaches will become apparent to one of skill in the art, through comparison of such systems with some aspects of the present invention as set forth in the remainder of the present application.

SUMMARY OF THE INVENTION

Certain embodiments of the present technology provide conformable eartips, substantially as shown in and/or described in connection with at least one of the figures.

These and other advantages, aspects and novel features of the present invention, as well as details of an illustrated embodiment thereof, will be more fully understood from the following description and drawings.

BRIEF DESCRIPTION OF THE DRAWING(S)

Figure 1:
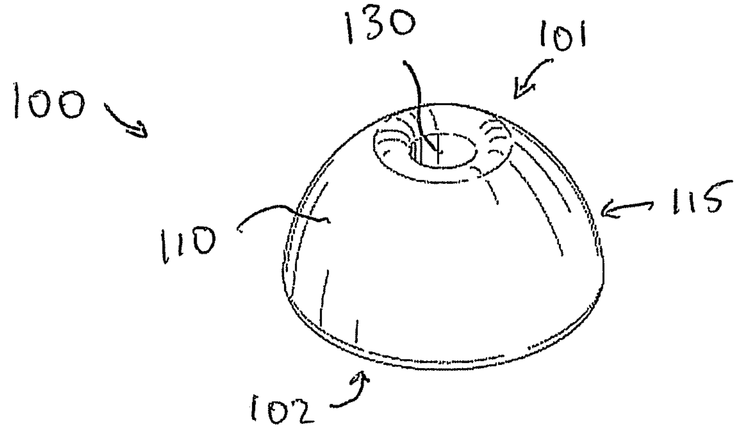
FIG. 1 depicts a top perspective view of an exemplary conformable eartip used in accordance with embodiments of the present technology.

The foregoing summary, as well as the following detailed description of embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF PREFERRED EMBODIMENT(S)

Embodiments of the present technology provide an eartip that conforms to the various shapes of human ear canals and provides an acoustic and pressure seal to the ear canal. The conformable eartip provides a low coefficient of friction so that the eartip inserts into the ear canal without discomfort and allows for direct insertion into the ear canal without requiring preparatory compression of the foam. The conformable eartip creates a minimal amount of pressure against the ear canal when inserted, has the ability to significantly distort its shape to easily conform to non-circular ear canal shapes, conforms to bends in an ear canal, and provides a seal at varying depths within an ear canal.

Various embodiments provide a conformable eartip 100 comprising a round flange 110 and a core 120. The round flange comprises a sealing surface 115 for mating with walls of an ear canal. The round flange 110 extends from an insertion end 101 to an opposite end 102 of the conformable eartip 100. The sealing surface 115 is tapered from the opposite end 102 toward the insertion end 101 of the conformable eartip 100. The core 120 is joined to the round flange 110 at the insertion end 101 of the conformable eartip 100. In various embodiments, the core 120 may extend from the insertion end 101 to a base 125 of the core 120 toward the opposite end 102 of the conformable eartip 100. The amount of extension of the core 120 can vary in certain embodiments, as illustrated in FIG. 4B compared to FIG. 9, for example. The core 120 includes a channel 125 extending through the core 120 from the insertion end 101 of the conformable eartip 100 to the base 125 of the core 120. In various embodiments, the conformable eartip 100 provides an elongation ratio, E, of at least 1.4 and/or a compression ratio, C, of at least 2.0.

Figure 2:
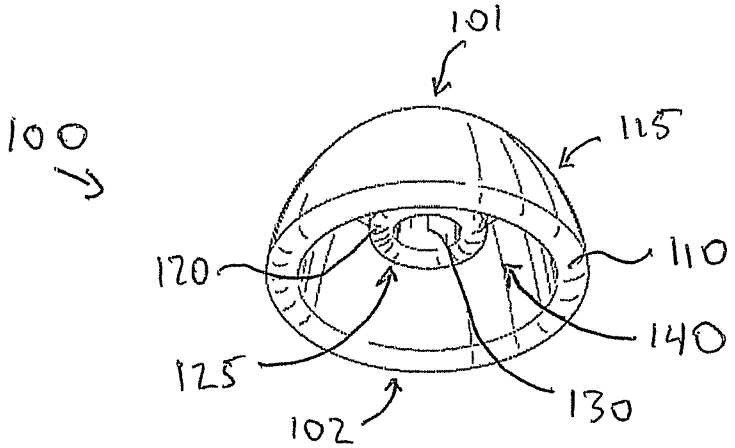
FIG. 2 depicts a bottom perspective view of an exemplary conformable eartip used in accordance with embodiments of the present technology.
Figure 3:
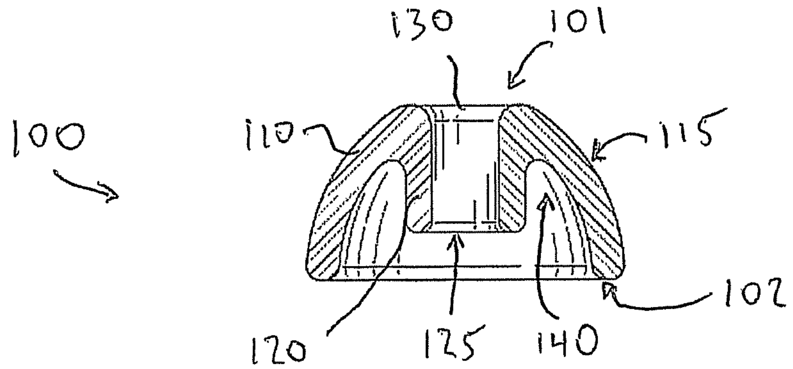
FIG. 3 depicts a cross-sectional side elevation view of an exemplary conformable eartip used in accordance with embodiments of the present technology.

FIG. 1 depicts a top perspective view of an exemplary conformable eartip 100 used in accordance with embodiments of the present technology. FIG. 2 depicts a bottom perspective view of an exemplary conformable eartip 100 used in accordance with embodiments of the present technology. FIG. 3 depicts a cross-sectional side elevation view of an exemplary conformable eartip 100 used in accordance with embodiments of the present technology.

Referring to FIGS. 1-3, there is shown an exemplary conformable eartip 100 comprising a flange 110 that is integrated with or fixably attached to a core 120. In various embodiments, the conformable eartip 100 can be high-density closed-cell polyurethane foam, silicone or other elastomeric foam, open-cell foam that has a surface sealing coating, or any suitable foam material that provides an acoustic and pressure seal to an ear canal. In embodiments where a pressure seal is not needed, the conformable eartip 100 may be open-cell foam or any suitable foam material that provides an acoustic seal, for example.

The flange 110 can be generally round and may provide a sealing surface 115 for mating with walls of an ear canal. The rounded shape of the flange 110 can reduce the tendency of the flange 110 to crease inward, causing leakage, for example. The flange 110 can be formed by hollowing out a section 140 between the flange 110 and the core 120 to allow the flange 110 to freely compress and elongate for conforming to an ear canal of a wearer. The flange 110 can extend a distance from an insertion end of the eartip 100 and may be tapered at an angle for ease of insertion as discussed in more detail below, for example. In various embodiments, the thickness of the flange may be as much as 30% of the outer diameter of the eartip or thinner, for example. The thin flange wall increases the range of conformance of the eartip 100 and allows the eartip 100 to conform and seal to the ear canal without applying a significant pressure against the ear canal wall, providing a more comfortable fit. The thin flange wall in conjunction with the length of extension of the flange 110 from the core 120 (e.g., the hollowed-out section 140) enables the eartip 100 to compress and extend more completely than existing eartips. In various embodiments, the flange wall can have a substantially uniform thickness.

Figure 4B:
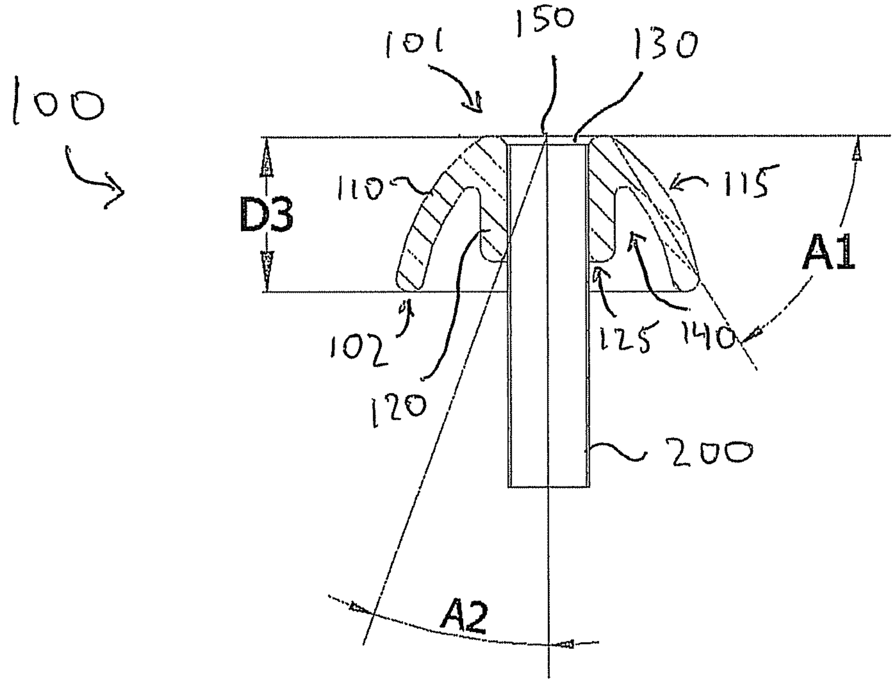
FIG. 4B depicts a cross-sectional side elevation view of an exemplary conformable eartip coupled to a sound tube used in accordance with embodiments of the present technology.
Figure 5:
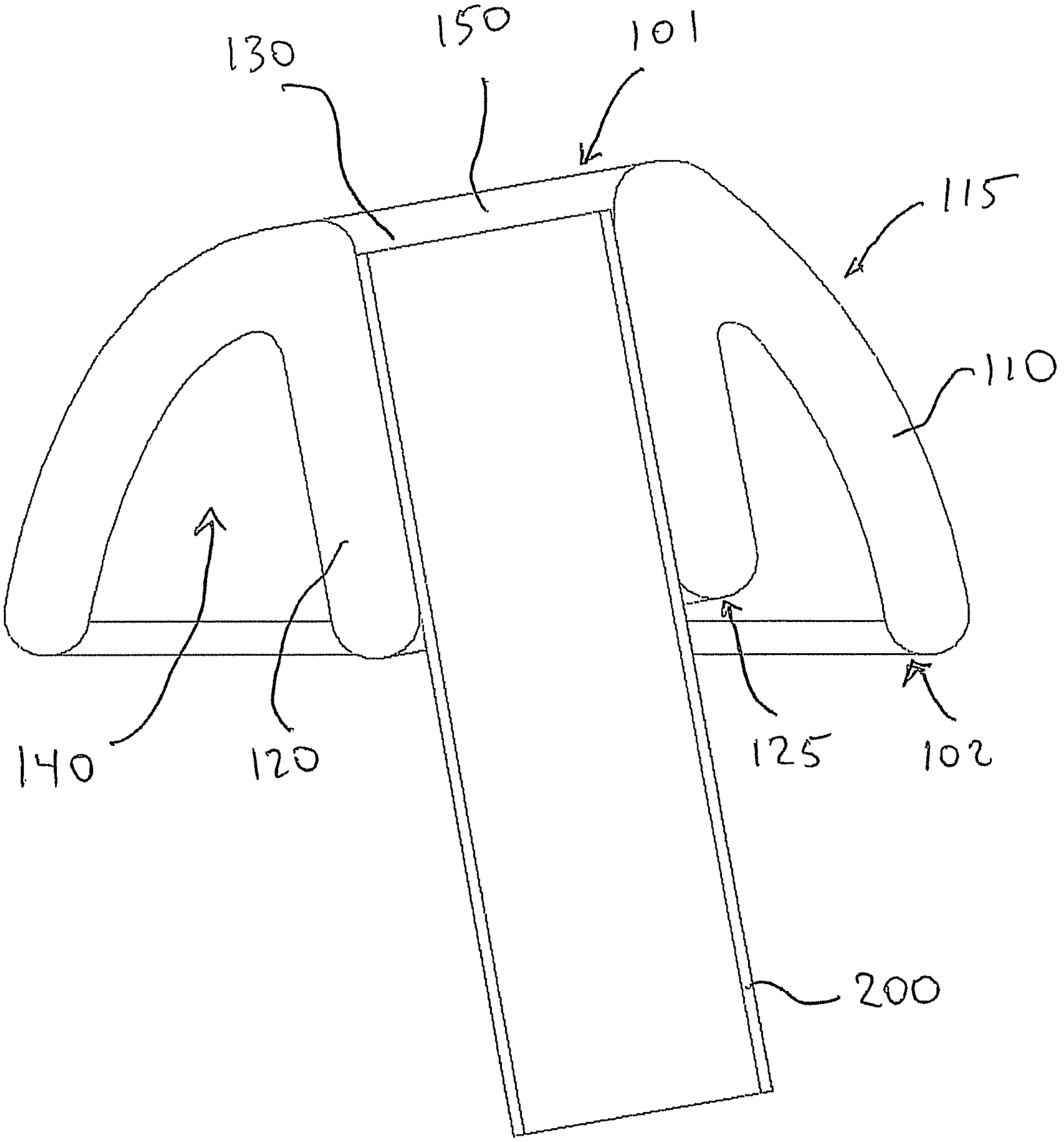
FIG. 5 depicts a cross-sectional side elevation view illustrating an exemplary angular compliance of an exemplary conformable eartip coupled to a sound tube used in accordance with embodiments of the present technology.
Figure 9:
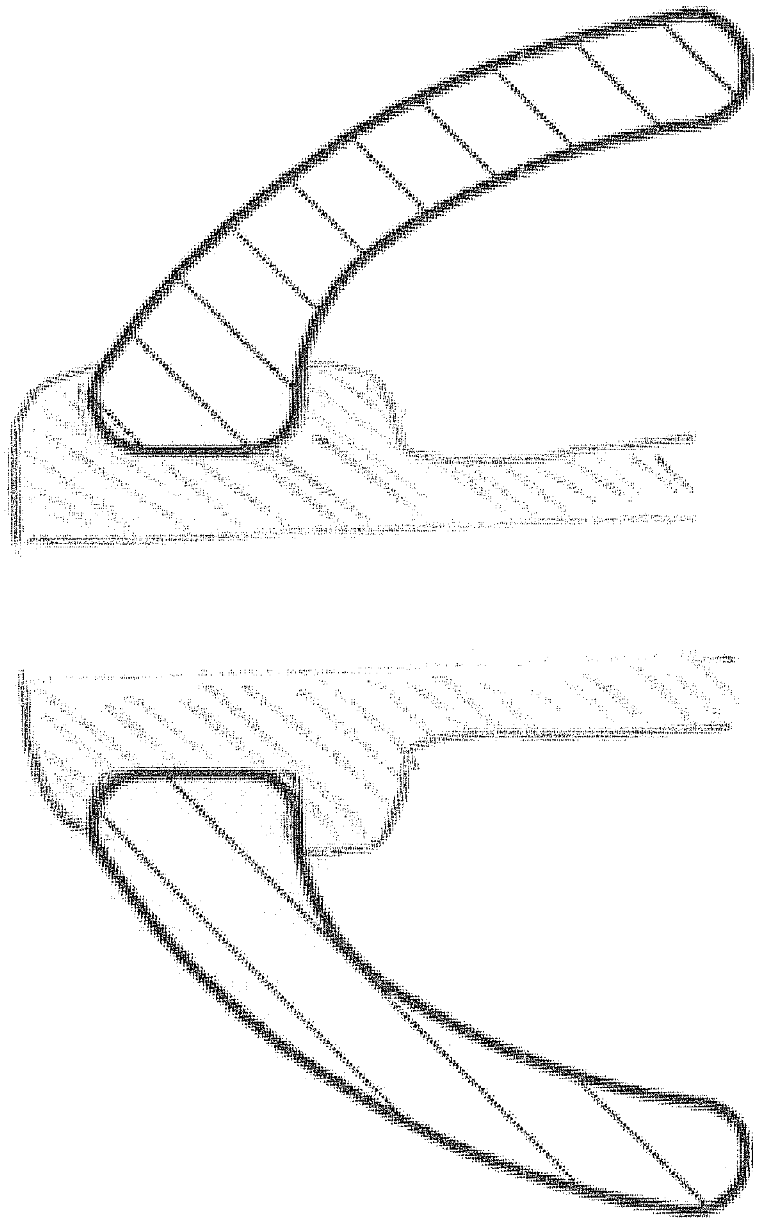
FIG. 9 depicts a cross-sectional side elevation view of an exemplary conformable eartip coupled to a hearing device used in accordance with embodiments of the present technology.

The core 120 may be generally round and can comprise a channel 130 extending through the core 120 from an insertion end 101 of the eartip 100 to a base 125 of the core 120. In various embodiments, the channel 130 of the core 120 can receive a tube or stem 200, as illustrated in FIGS. 4B and 5, for example. The tube or stem 200 can be affixed in the channel by an adhesive such as a room temperature vulcanizing (RTV) silicone rubber adhesive, other adhesive, solvent bonded, or insert molded, among other things. Alternatively, the eartip may be affixed directly to a hearing device, as illustrated in FIG. 9, for example. In various embodiments, the tube or stem 200 can attach to a hearing device, such as an audio player earphone, a communications earphone, a hearing aid, a hearing testing apparatus, an earplug, or any suitable hearing device. In certain embodiments, a wall of the core 120 can have a substantially uniform thickness and/or have substantially the same thickness as the wall of the flange 110.

Figure 4A:
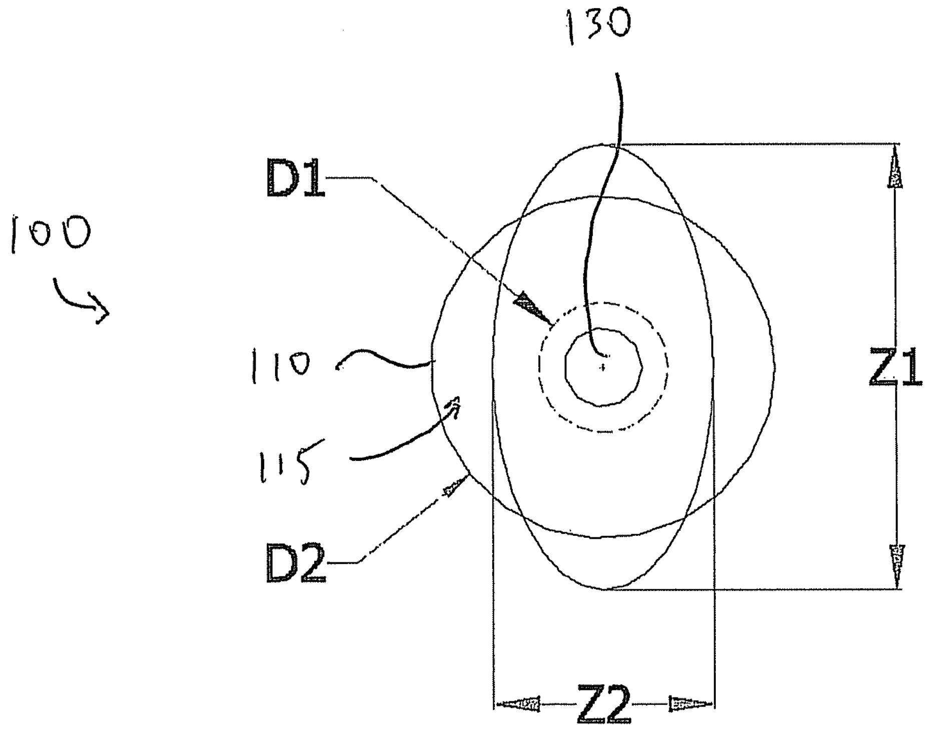
FIG. 4A depicts a top plan view of a relaxed state and a compressed state of an exemplary conformable eartip used in accordance with embodiments of the present technology.

FIG. 4A depicts a top plan view of a relaxed state and a compressed state of an exemplary conformable eartip 100 used in accordance with embodiments of the present technology. Referring to FIG. 4A, the ability of an eartip 100 to conform to an ear canal can be determined by the ratio of the maximum outer diameter (D2) of the sealing surface 115 of the flange 110 to the minimum width of the sealing surface 115 of the flange 110 under compression (Z2), but without compression of the eartip material, for example. This minimum width is defined as the diameter of the sound tube 200, plus 2 times the thickness of the core 120 wall, plus two times the thickness of the flange 110 wall. In other words, the compression ratio, C, equals D2/Z2. The compression ratio of an eartip 100 may indicate the narrowest dimension of an ear canal to which the eartip 100 comfortably fits, without causing significant pressure against the ear canal wall or distorting the ear canal, for example. The structure of the conformable eartip 100 provides thin walls of the flange 110 and a narrow core 120, allowing the flange 110 to collapse completely to the core 120, and resulting in a compression ratio of 2.0 or greater. The compression ratio of existing commercially available eartips measured ranged from 1.0 to 1.88.

The ability of an eartip 100 to seal to an ear canal can be determined based on the ability of the eartip 100 to elongate the sealing surface of the flange 110 to meet the profile of a typically elliptical ear canal. The elongation may be determined by a ratio of the maximum width of the sealing surface 115 of the flange 110 at full compression (Z1) with the maximum nominal outer diameter (D2) of the sealing surface 115 of the flange 110. In other words, the elongation ratio, E, equals Z1/D2. The conformable eartip 100 provides a hollowed out section 140 between the flange 110 and the core 120 that allows the eartip 100 to freely elongate from its relaxed state. In various embodiments, the conformable eartip 100 provides an elongation ratio, E, of 1.4 or greater. The elongation ratio, E, of existing available eartips measured ranged from 1.0 to 1.2.

FIG. 4B depicts a cross-sectional side elevation view of an exemplary conformable eartip 100 coupled to a sound tube 200 used in accordance with embodiments of the present technology. FIG. 5 depicts a cross-sectional side elevation view illustrating an exemplary angular compliance, A2, of an exemplary conformable eartip 100 coupled to a sound tube 200 used in accordance with embodiments of the present technology.

Referring to FIGS. 4B and 5, the ability of an eartip to adapt to a bend in the ear canal may be determined by measuring the amount of deflection (A2), with a given axial load at a stem or sound tube 200, of the sealing surface 115 of the flange 110 with respect to the stem or sound tube 200. The deflection (A2) of the eartip 100 allows the sealing surface 115 of the flange 110 to mate with ear canal walls of a wearer in the same manner as it would without or before an ear canal bend. Human ear canals typically have a bend along the length of the canal. An eartip that is unable to accommodate a bend in the ear canal can have difficulty sealing properly unless it distorts the ear canal walls to meet the sealing surface of the tip. In various embodiments, the sealing surface 115 of the flange 110 deflects at a hinge point 150 at an ear canal insertion end 101 of the eartip 100 from a nominal angle to the sound tube 200 such that the eartip 100 may readily conform the shape of the sealing surface 115 to maintain a seal to the ear canal as it bends, as illustrated in FIG. 5, for example. Aspects of the present invention provide a conformable eartip with an angular compliance (A2) of up to 45 degrees. For example, various embodiments provide a maximum angular compliance (A2) between 20 and 45 degrees, or any range therebetween. Existing available eartips measured a maximum angular compliance (A2) of less than 20 degrees.

Certain embodiments provide that an eartip 100 can seal to an ear canal of a wearer where the outer diameter, in either a nominal profile (D2) or distorted to match the profile of the ear canal, is of sufficient size to at least match the diameter or effective diameter of the ear canal. The maximum outer diameter of the eartip sealing surface is, in common practice, not directly at the insertion end 101 of the eartip 100 but at some distance (D3) behind the insertion end 101 of the eartip 100. In various embodiments, the distance (D3) can define a minimum insertion depth for sealing the eartip 100 in the ear canal, where shorter minimum insertions depths may provide a more versatile eartip. In certain embodiments, the distance (D3) may not be less than the maximum eartip diameter (D2) minus the minimum eartip diameter (D1) over the effective taper angle (A1) of the eartip 100.

Referring to FIG. 4B, the ease of which a particular eartip may be inserted into an ear canal may be defined by three aspects: the friction coefficient of the material, the need for pre-insertion activity, and the taper angle (A1) of the sealing surface 115 of the flange 110. Various embodiments provide that the eartip 100 is composed of materials that have a low friction coefficient, such as high-density closed-cell polyurethane foam, silicone or other elastomeric foam, open-cell foam, or the like.

Regarding pre-insertion activity, when additional steps are needed prior to inserting an eartip into an ear canal of a wearer, the additional steps can make the insertion process generally more difficult and/or complicated. For example, aligning an eartip to a particular orientation, adding lubricant to an eartip, and/or pre-forming the eartip by compressing the foam to reduce the outer diameter is generally more difficult and/or complicated than inserting an eartip without pre-insertion activity. Various embodiments provide that the eartip 100 is inserted into an ear canal of a wearer without performing pre-insertion activity.

The taper angle (A1) of the sealing surface of the flange 110 defines a shape of the eartip 100 that impacts the ease of insertion of the eartip 100 into an ear canal of a wearer. The taper angle (A1) of the sealing surface of the flange 110 can be determined by the following formula:

$$A1 = \tan^{-1}\frac{D3}{\left(\frac{D2 - D1}{2}\right)}$$

where D3 is the distance between the insertion end 101 of the eartip 100 and an opposite end 102 of the flange 110 (as illustrated in FIG. 4B), D1 is the minimum eartip 100 diameter (as illustrated in FIG. 4A), and D2 is the maximum eartip 100 diameter (as illustrated in FIG. 4A). In various embodiments, the minimum eartip diameter (D1) can be the outer diameter of the core 120, for example. Aspects of the present invention provide that a taper angle (A1) of the sealing surface of the flange 110 is at least 45 degrees to enable conformability and less than 75 degrees so that the flange 110 taper is shallow enough to enable sealing at a short distance.

Figure 6:
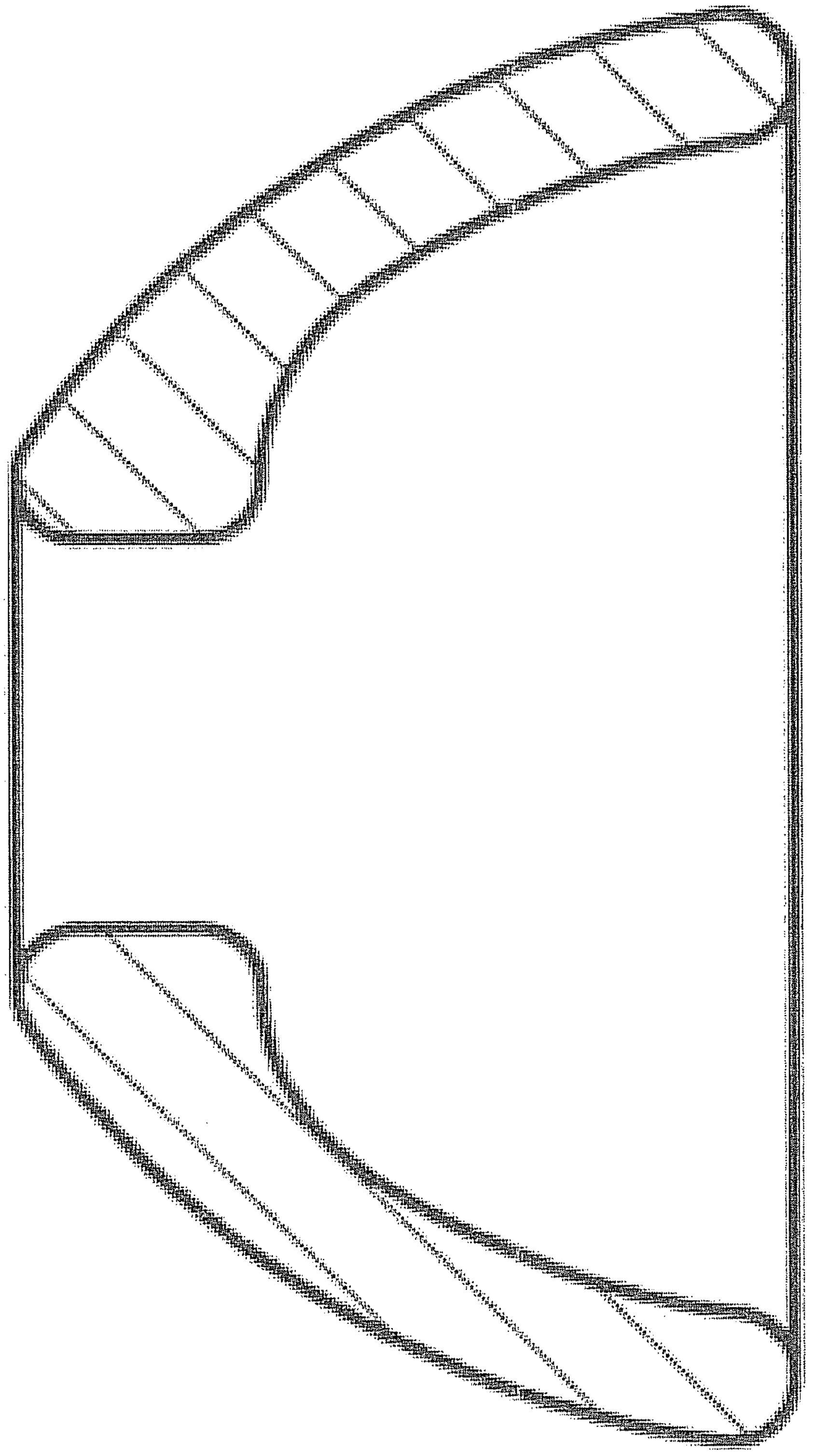
FIG. 6 depicts a cross-sectional side elevation view of an exemplary conformable eartip used in accordance with embodiments of the present technology.
Figure 7:
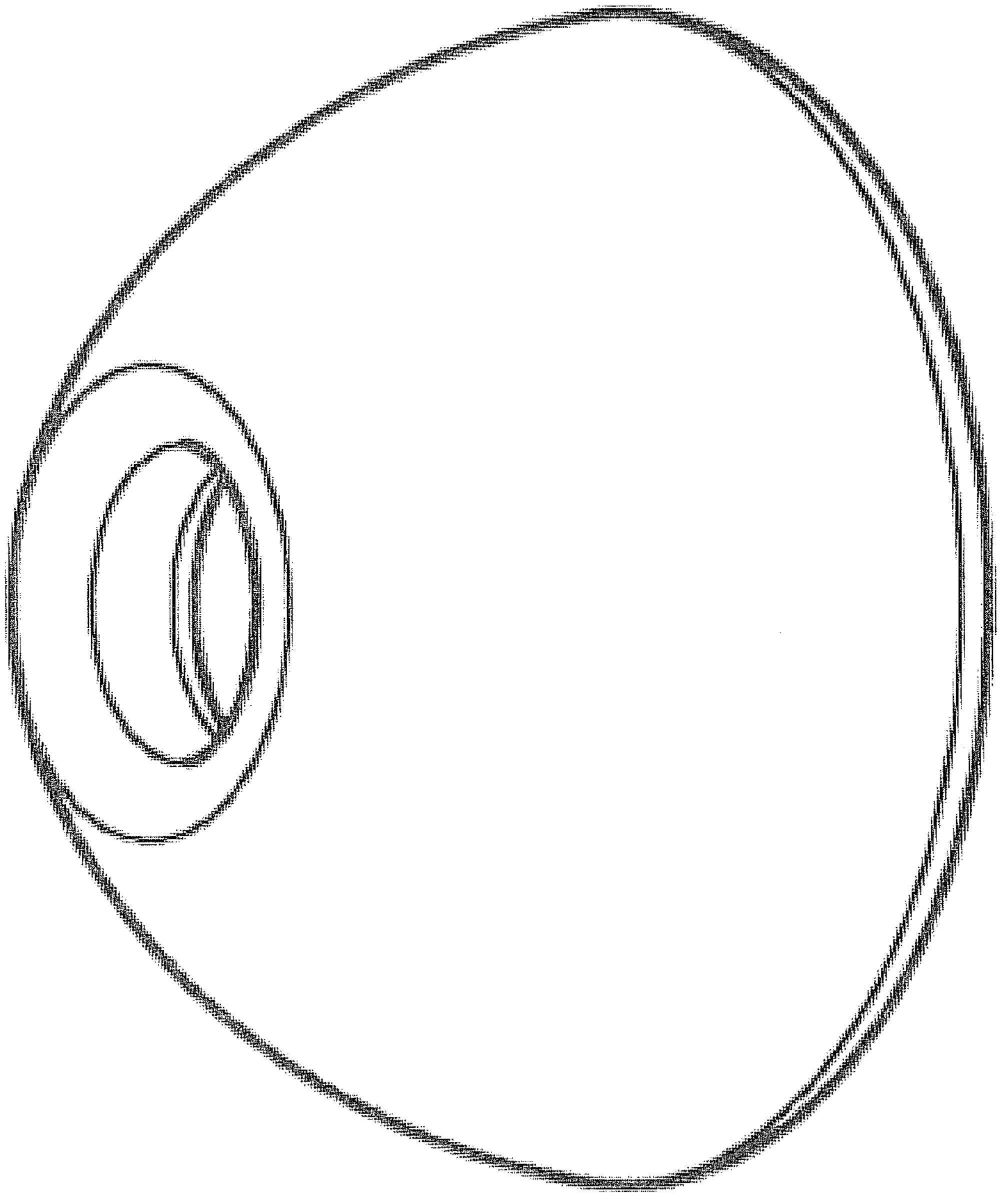
FIG. 7 depicts a top perspective view of an exemplary conformable eartip used in accordance with embodiments of the present technology.
Figure 8:
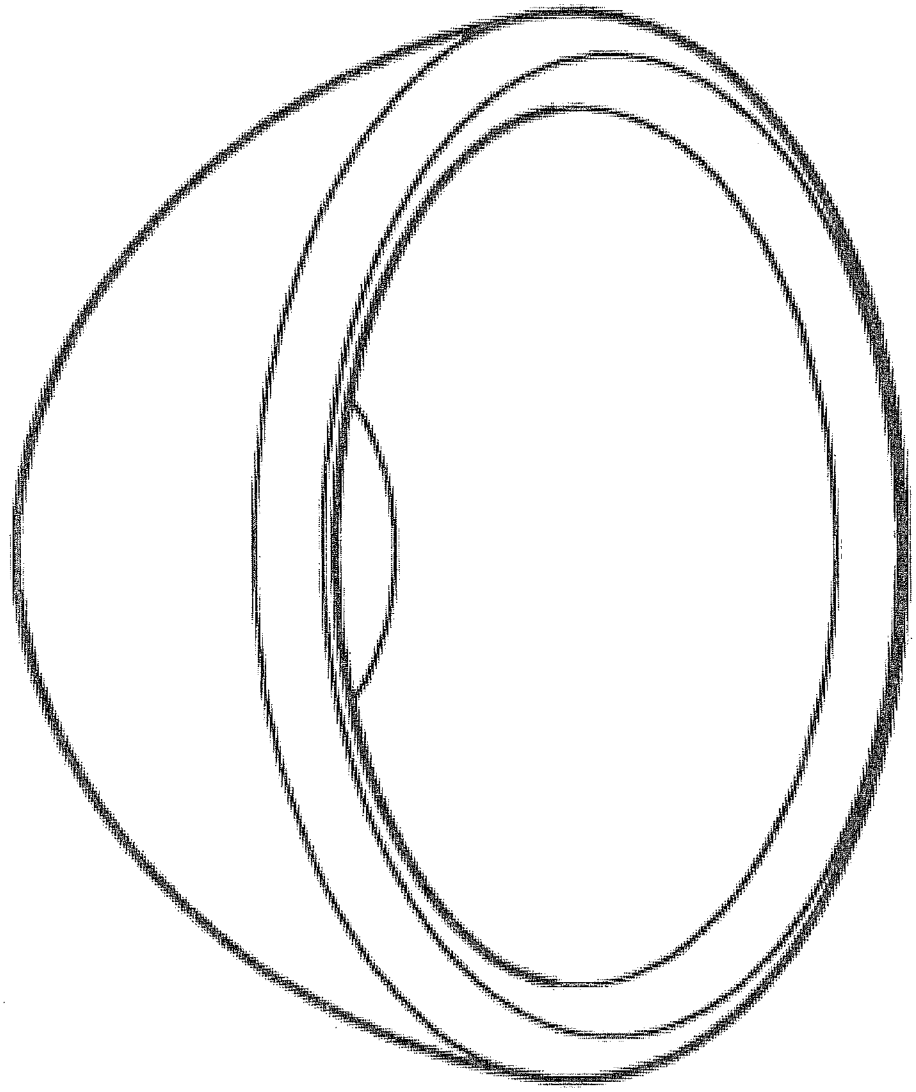
FIG. 8 depicts a bottom perspective view of an exemplary conformable eartip used in accordance with embodiments of the present technology.
Figure 10:
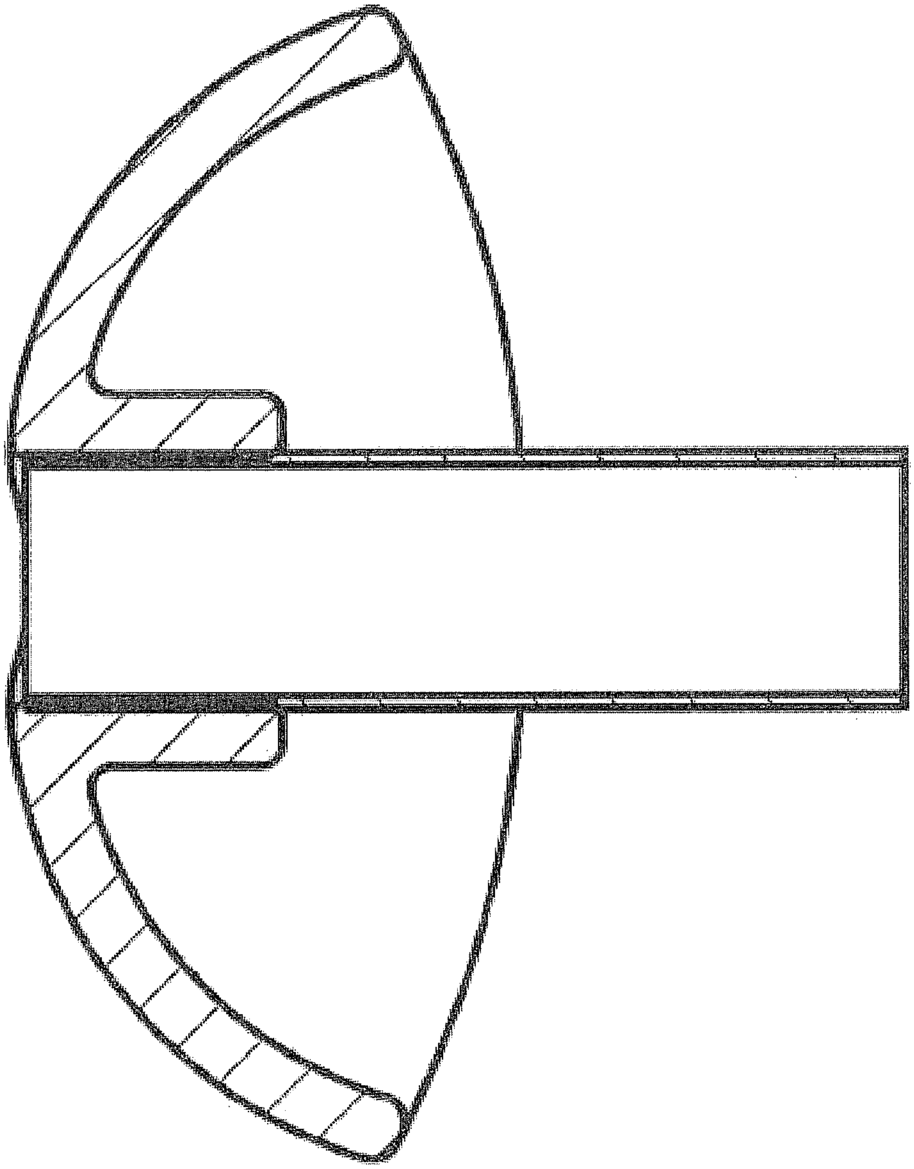
FIG. 10 depicts a cross-sectional side elevation view of an exemplary elongated conformable eartip coupled to a sound tube used in accordance with embodiments of the present technology.
Figure 11:
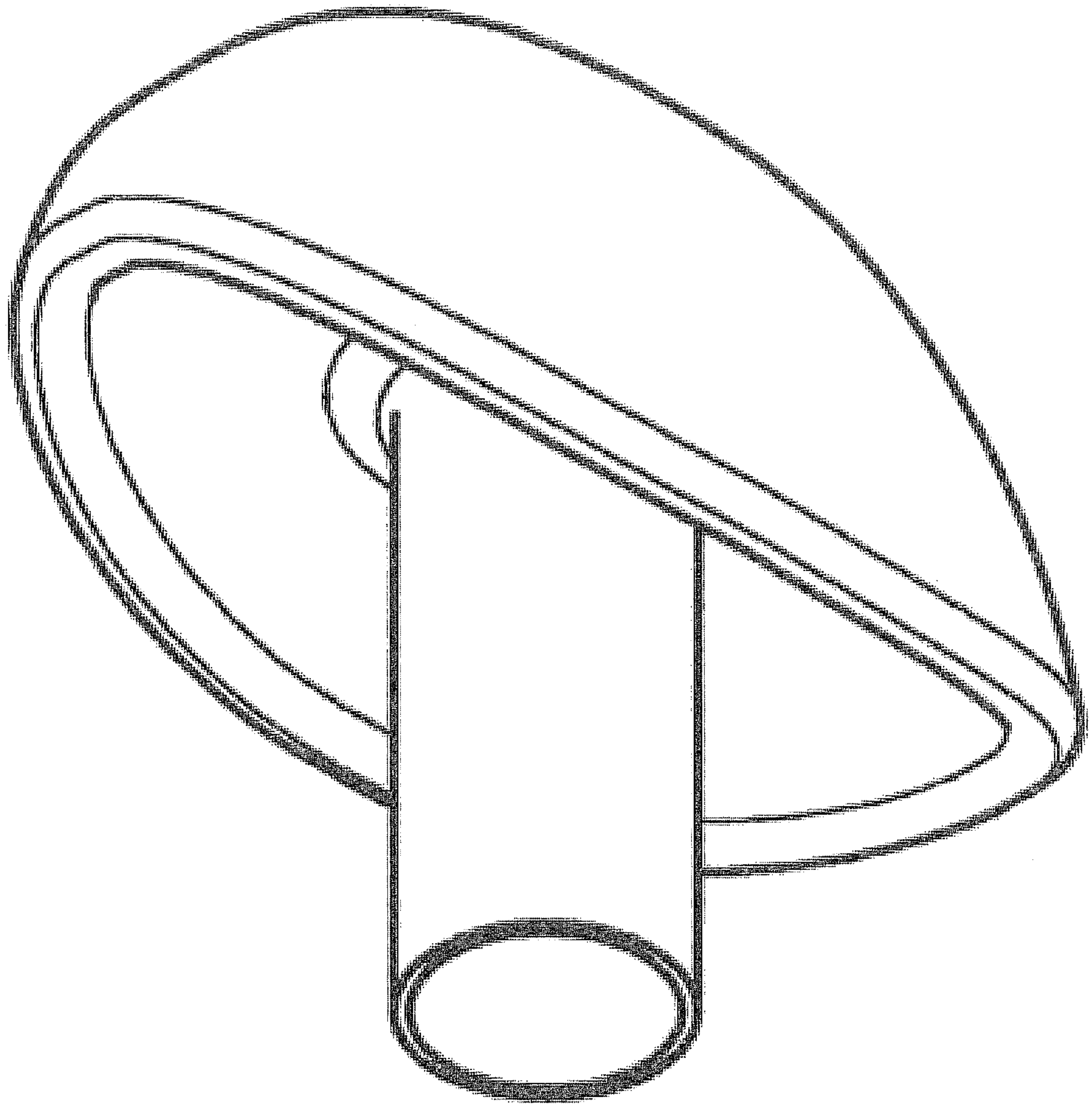
FIG. 11 depicts a bottom perspective view of an exemplary conformable eartip that is conforming by compressing and elongating as used in accordance with embodiments of the present technology.
Figure 12:
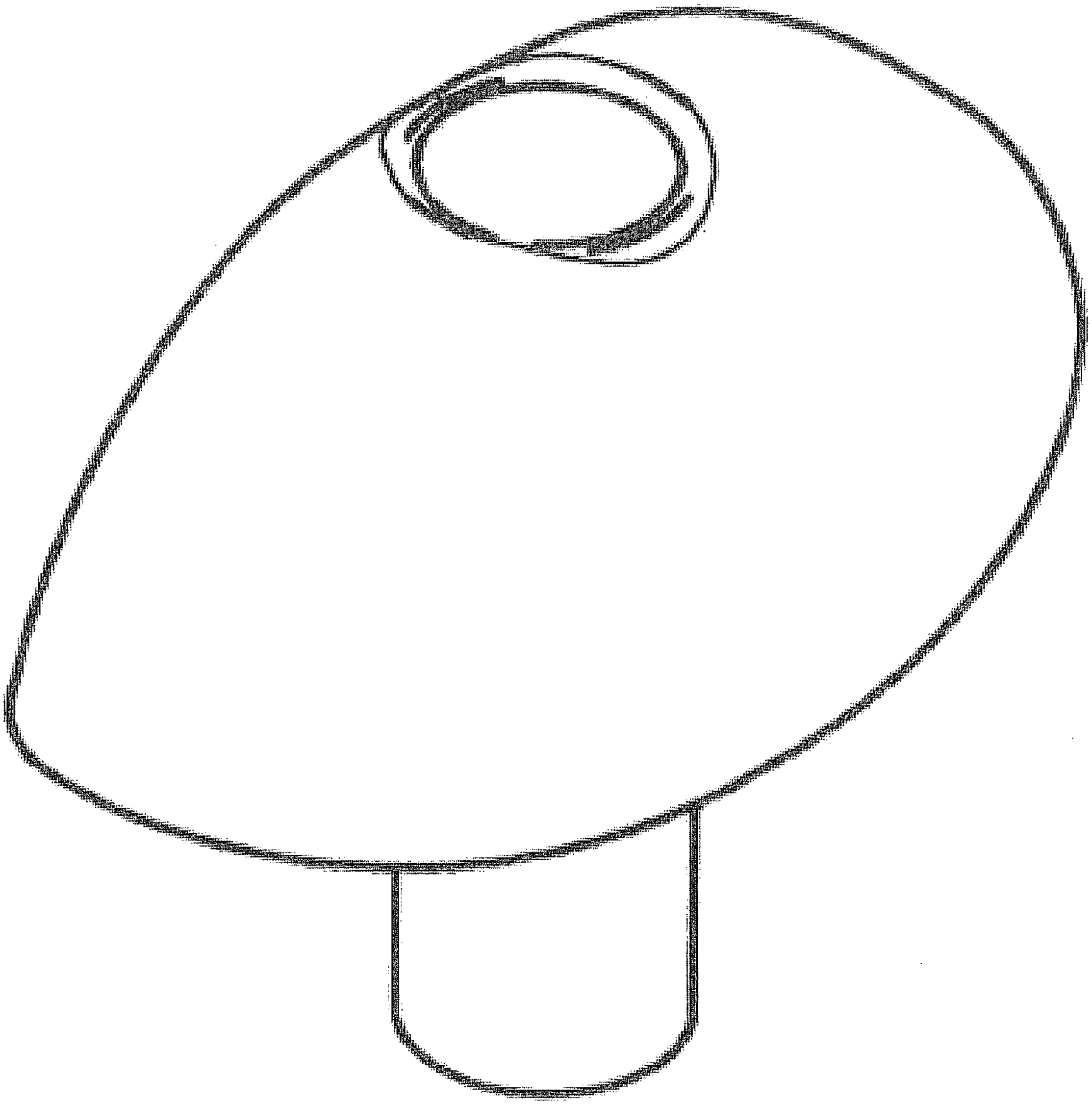
FIG. 12 depicts a top perspective view of an exemplary conformable eartip that is conforming by compressing and elongating as used in accordance with embodiments of the present technology.
Figure 13:
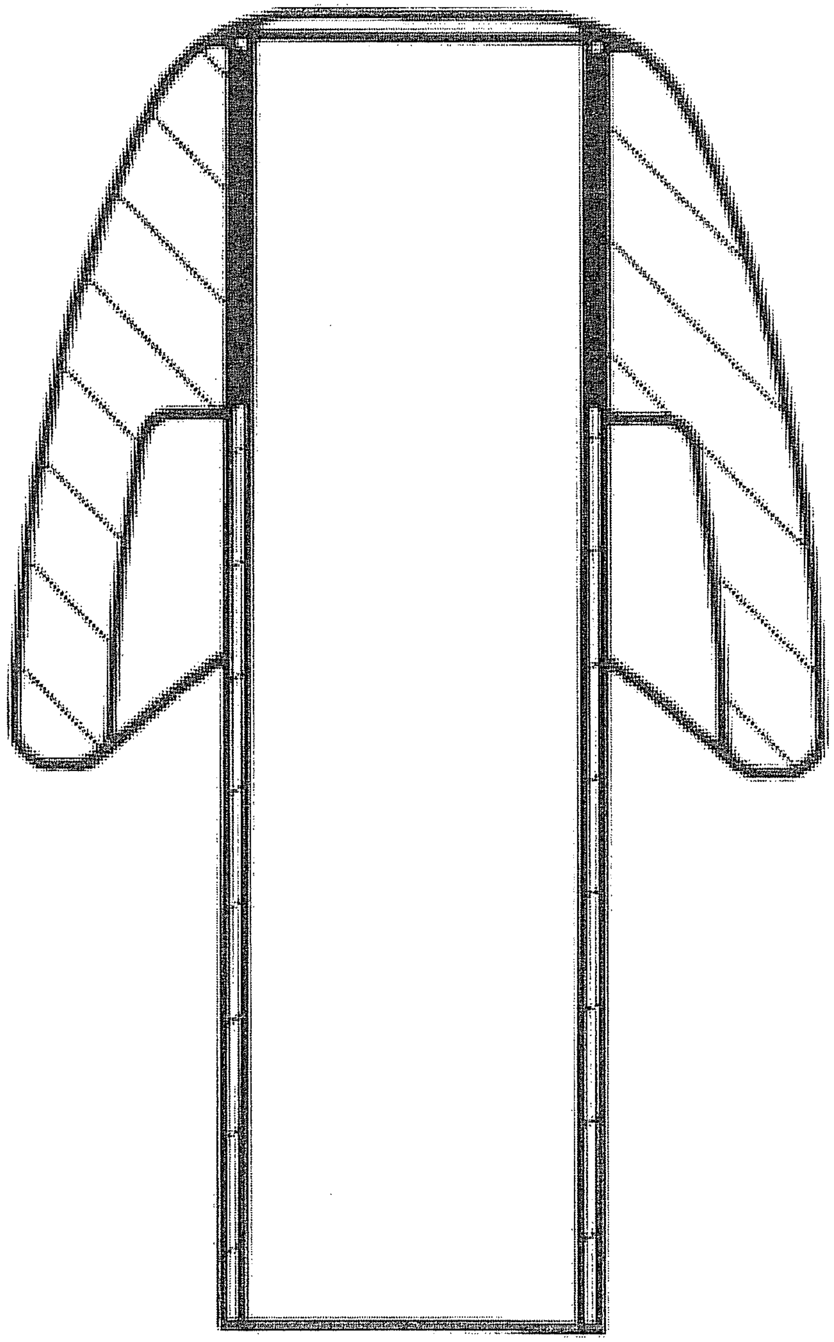
FIG. 13 depicts a cross-sectional side elevation view of an exemplary compressed conformable eartip coupled to a sound tube used in accordance with embodiments of the present technology.

FIG. 6 depicts a cross-sectional side elevation view of an exemplary conformable eartip used in accordance with embodiments of the present technology. FIG. 7 depicts a top perspective view of an exemplary conformable eartip used in accordance with embodiments of the present technology. FIG. 8 depicts a bottom perspective view of an exemplary conformable eartip used in accordance with embodiments of the present technology. FIG. 9 depicts a cross-sectional side elevation view of an exemplary conformable eartip coupled to a hearing device used in accordance with embodiments of the present technology. FIG. 10 depicts a cross-sectional side elevation view of an exemplary elongated conformable eartip coupled to a sound tube used in accordance with embodiments of the present technology. FIG. 11 depicts a bottom perspective view of an exemplary conformable eartip that is conforming by compressing and elongating as used in accordance with embodiments of the present technology. FIG. 12 depicts a top perspective view of an exemplary conformable eartip that is conforming by compressing and elongating as used in accordance with embodiments of the present technology. FIG. 13 depicts a cross-sectional side elevation view of an exemplary compressed conformable eartip coupled to a sound tube used in accordance with embodiments of the present technology.

The conformable eartip 100 illustrated in FIGS. 6-13 share various characteristics with the conformable eartip 100 illustrated in FIGS. 1-5 as described above.

In a representative embodiment, a conformable eartip 100 is provided that comprises a round flange 110 and a core 120. The round flange includes a sealing surface 115 for mating with walls of an ear canal. The round flange 110 extends from an insertion end 101 to an opposite end 102 of the conformable eartip 100. The sealing surface 115 is tapered from the opposite end 102 toward the insertion end 101 of the conformable eartip 100. The core 120 is joined to the round flange 110 at the insertion end 101 of the conformable eartip 100. The core 120 extends from the insertion end 101 to a base 125 of the core 120 toward the opposite end 102 of the conformable eartip 100. The core 120 includes a channel 125 extending through the core 120 from the insertion end 101 of the conformable eartip 100 to the base 125 of the core 120. In various embodiments, the conformable eartip 100 provides an elongation ratio, E, of at least 1.4 and/or a compression ratio, C, of at least 2.0.

While particular elements, embodiments and applications of the present invention have been shown and described, it will be understood that the invention is not limited thereto since modifications can be made by those skilled in the art without departing from the scope of the present disclosure, particularly in light of the foregoing teachings.

What is claimed is:

1. A conformable eartip comprising:

a round flange comprising a sealing surface arranged to mate with walls of an ear canal, wherein the round flange extends from an insertion end to an opposite end of the conformable eartip, wherein the sealing surface is tapered from the opposite end toward the insertion end of the conformable eartip, wherein the sealing surface comprises a maximum outside diameter at a relaxed state, D2, and a maximum width at a compressed state, Z1; and a core joined to the round flange at the insertion end of the conformable eartip, the core extending from the insertion end to a base of the core toward the opposite end of the conformable eartip, the core comprising a channel extending through the core from the insertion end of the conformable eartip to the base of the core, wherein the round flange and the core is at least one of: high-density closed-cell foam, and open-cell foam comprising a surface sealing coating.

2. The conformable eartip of claim 1, wherein a thickness of the round flange is less than about 30% of the maximum outside diameter at the relaxed state, D2.

3. The conformable eartip of claim 1, comprising a hollowed-out section between the round flange and the core.

4. The conformable eartip of claim 1, wherein the conformable eartip provides an elongation ratio, E, of at least 1.4, the elongation ratio, E, defined by the formula:

$$E = \frac{Z1}{D2}.$$

5. The conformable eartip of claim 1:

wherein the sealing surface comprises a minimum width at a compressed state, Z2; and wherein the conformable eartip provides a compression ratio, C, of at least 2.0, the compression ratio, C, defined by the formula:

$$C = \frac{D2}{Z2}.$$

6. The conformable eartip of claim 1, comprising a stem or a sound tube that extends through and attaches to the channel of the core.

7. The conformable eartip of claim 6, comprising a hinge point at the insertion end, wherein the sealing surface deflects at the hinge point at an angle up to between 20 and 45 degrees from the stem or the sound tube when a given axial load is provided at the stem or the sound tube.

8. The conformable eartip of claim 6, wherein the stem or the sound tube is attached to the channel with an adhesive.

9. The conformable eartip of claim 1, wherein the round flange is substantially a uniform thickness.

10. The conformable eartip of claim 1, wherein the core is substantially a uniform thickness.

11. The conformable eartip of claim 1, wherein the round flange and the core is substantially a uniform thickness.

12. The conformable eartip of claim 1, wherein the conformable eartip is inserted into an ear canal of a wearer without performing pre-insertion activities.

13. The conformable eartip of claim 1, wherein the sealing surface is tapered from the opposite end toward the insertion end of the conformable eartip at an angle, A1, that is between 45 and 75 degrees, the angle, A1, defined by the formula:

$$A1 = \tan^{-1}\frac{D3}{\left(\frac{D2 - D1}{2}\right)},$$

where D3 is the distance along the core that the round flange extends from the insertion end to the opposite end of the conformable eartip, and D1 is an outer diameter of the core at the relaxed state.

* * * * *